United States Patent [19]

Noujaim et al.

[11] Patent Number: 5,203,335

[45] Date of Patent: Apr. 20, 1993

[54] PHASED ARRAY ULTRASONIC BEAM FORMING USING OVERSAMPLED A/D CONVERTERS

[75] Inventors: Sharbel E. Noujaim, Clifton Park; Steven L. Garverick, Schenectady, both of N.Y.; Matthew O'Donnell, Ann Arbor, Mich.

[73] Assignee: General Electric Company, Schenectady, N.Y.

[21] Appl. No.: 844,031

[22] Filed: Mar. 2, 1992

[51] Int. Cl.[5] ............................................. A61B 8/12
[52] U.S. Cl. ................................ 128/661.01; 73/625
[58] Field of Search ............... 128/660.01, 660.07, 128/661.01; 364/413.13, 413.25; 73/861.25, 861.26, 627, 628, 625, 626

[56] References Cited

U.S. PATENT DOCUMENTS

| | | | |
|---|---|---|---|
| 4,254,662 | 3/1981 | Kuroda et al. | 128/661.01 |
| 4,989,143 | 1/1991 | O'Donnell et al. | 128/661.01 |
| 5,005,419 | 4/1991 | O'Donnell et al. | 128/661.01 |
| 5,014,712 | 5/1991 | O'Donnell | 128/661.01 |
| 5,030,954 | 7/1991 | Ribner | 341/172 |
| 5,065,157 | 11/1991 | Ribner et al. | 341/143 |
| 5,084,702 | 1/1992 | Ribner | 341/143 |
| 5,103,229 | 4/1992 | Ribner | 341/143 |

OTHER PUBLICATIONS

S. C. Leavitt et al., "A Scan Conversion Algorithm for Displaying Ultrasound Images", Hewlett-Packard Journal, Oct. 1983, pp. 30–34.

E. Dijkstra et al., "A Design Methodology For Decimation Filters In Sigma-Delta A/D Converters", ISCAS 87, pp. 479–482 (1987).

E. Dijkstra et al., "On The Use of Modulo Arithmetic Comb Filters In Sigma-Delta Modulators", IEEE, pp. 2001–2004 (1988).

Primary Examiner—William E. Kamm
Assistant Examiner—George Manuel
Attorney, Agent, or Firm—Marvin Snyder

[57] ABSTRACT

A beam former in a PASS ultrasonic imaging system includes a set of sigma-delta modulators which operate to separately digitize the received echo signal from each transducer element. The oversampled one-bit digital representations of each echo signal are delayed as required for beam steering and focusing, and are summed together. A decimator filter reduces the sample rate of the digitized receive beam prior to display of the image resulting from the receive beam.

12 Claims, 6 Drawing Sheets

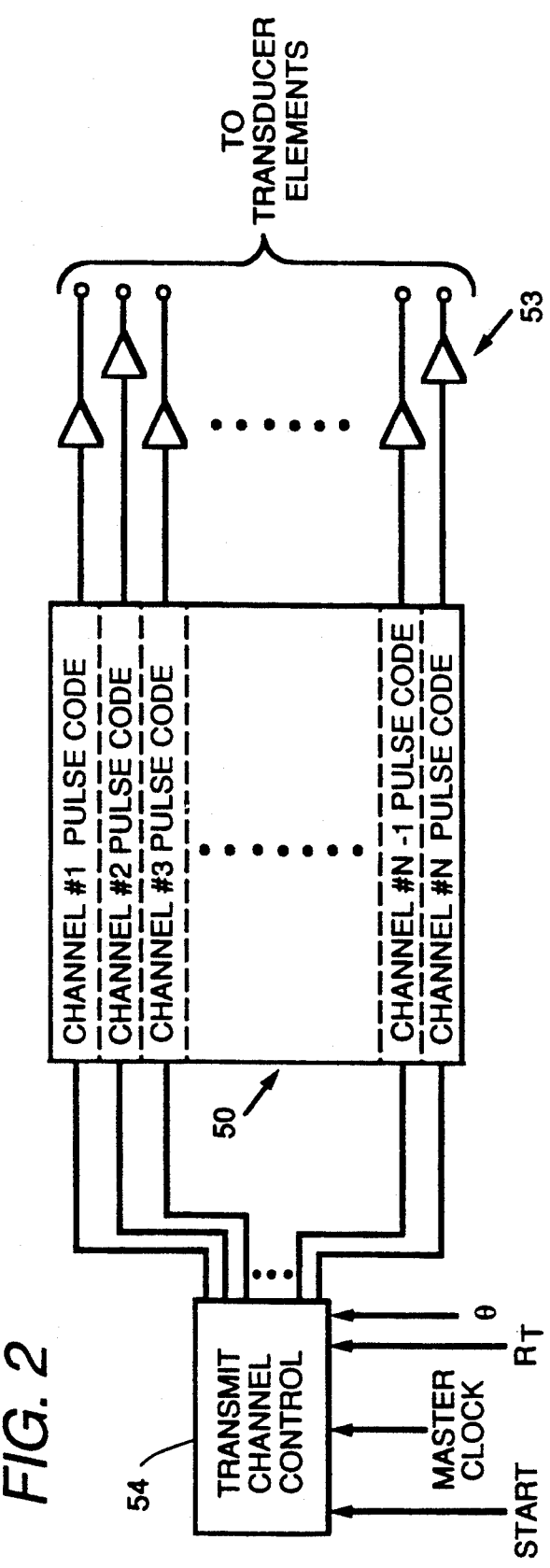
FIG. 2
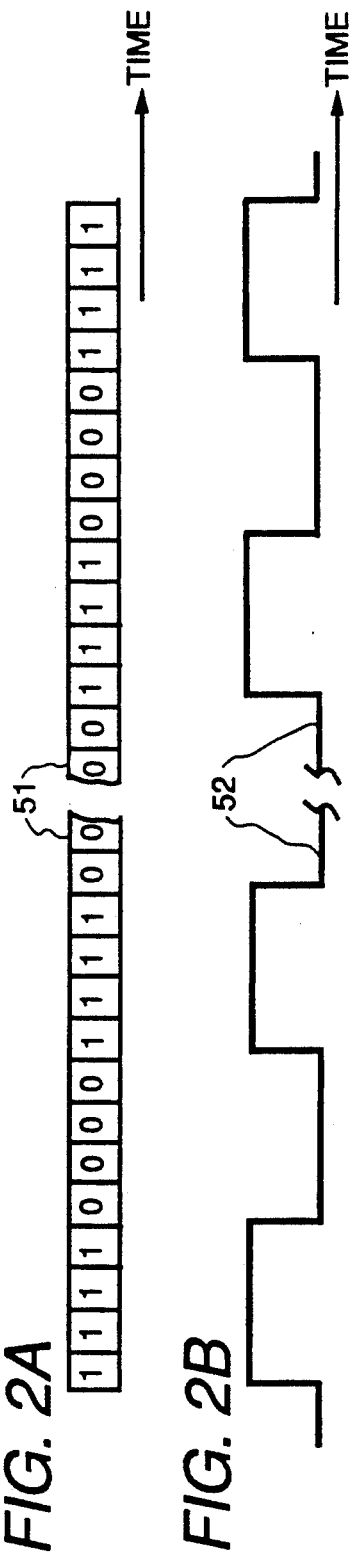
FIG. 2A
FIG. 2B

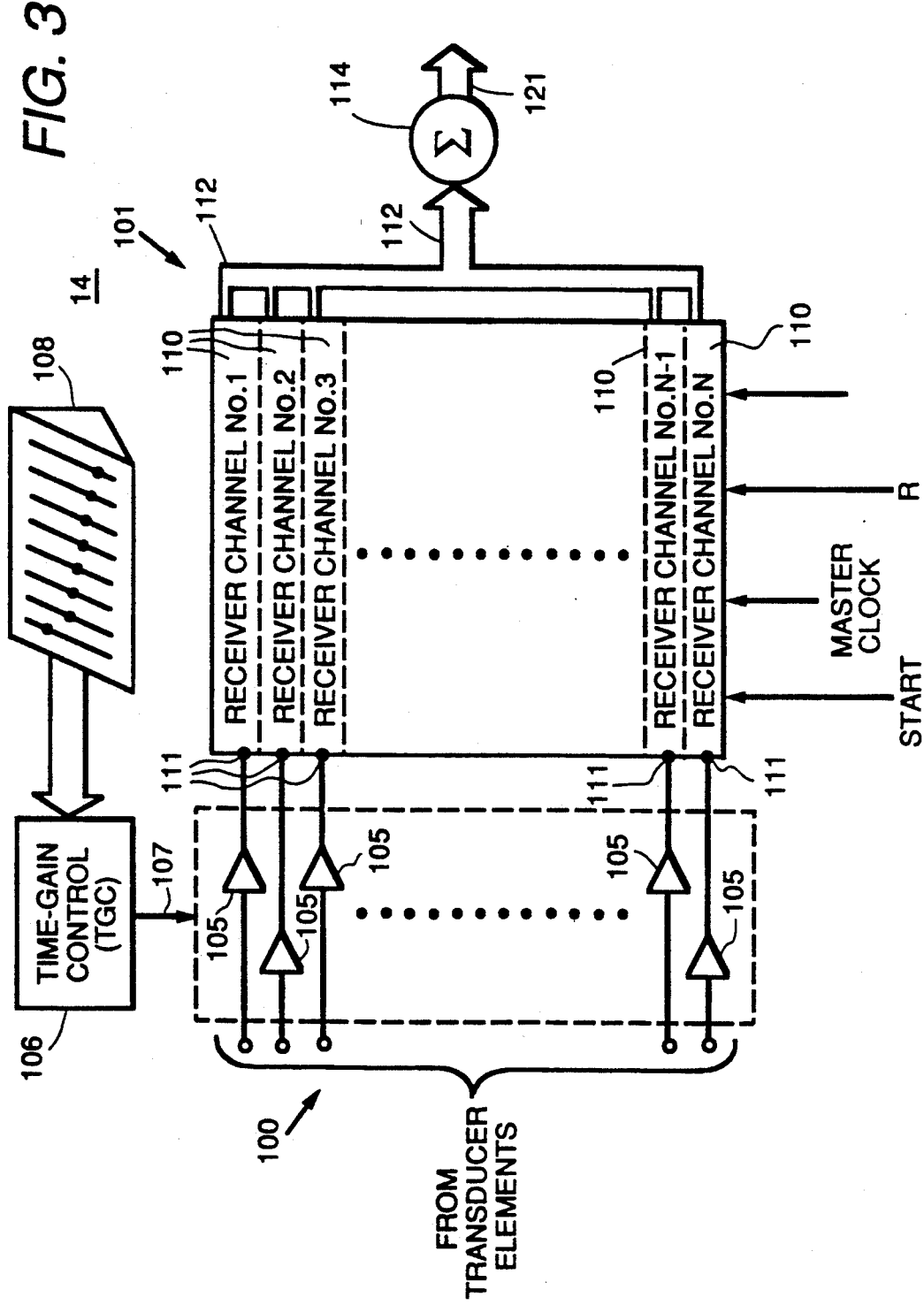

PHASED ARRAY ULTRASONIC BEAM FORMING USING OVERSAMPLED A/D CONVERTERS

BACKGROUND OF THE INVENTION

This invention relates to coherent imaging systems using vibratory energy, such as ultrasound and, in particular, to an ultrasound imaging system in which a focused and steered beam is produced by delaying the signals produced by the separate elements of a transducer array.

There are a number of modes in which vibratory energy, such as ultrasound, can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("reflection", "backscatter" or "echo" mode). The present invention relates to a backscatter method for producing ultrasound images.

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

In the so-called C-scan method, the transducer is scanned across a plane above the object and only the echoes reflecting from the focal depth of the transducer are recorded. The sweep of the electron beam of a CRT display is synchronized to the scanning of the transducer so that the x and y coordinates of the transducer correspond to the x and y coordinates of the image.

Ultrasonic transducers for medical applications are constructed from one or more piezoelectric elements sandwiched between a pair of electrodes. Such piezoelectric elements are typically constructed of lead zirconate titanate (PZT), polyvinylidene difluoride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231, all of which are assigned to the instant assignee.

When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved or "steered," in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and-/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction ($\theta$) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio. For example, a total of 128 scan lines may be acquired over a 90 degree sector, with each scan line being steered in increments of 0.70°. A number of such ultrasonic imaging systems are disclosed in U.S. Pat. Nos. 4,155,258; 4,155,260; 4,154,113; 4,155,259; 4,180,790; 4,470,303; 4,662,223; 4,669,314; 4,809,184; 4,796,236; 4,839,652 and 4,983,970, all of which are assigned to the instant assignee.

When forming a steered and focused beam from the ultrasonic echo signals received by each transducer element in the array, the signals produced by each transducer element must be delayed by a precise amount in order to compensate for the time of flight differences between the elements on the array. The accuracy with which these delays can be controlled impacts the quality of the final coherent sum of all the array element signals and, therefore, the quality of the resulting image. In medical ultrasonic imaging systems, a delay resolution of 1/32 of the wavelength of the transmitted ultrasonic frequency will provide the needed beam quality. For example, if a 5 MHz ultrasonic carrier frequency is employed, a delay resolution of 6.25 nanoseconds (1/32 (5 MHz)) is required.

In prior systems such as those described in the above-cited patents, such delay resolution in the beam forming circuitry of the ultrasonic receiver requires a large amount of hardware and consumes a large amount of power. The most recent designs sample each transducer element signal using highly accurate A/D converters which produce multi-bit digital numbers that indicate the in-phase and quadrature components of the sampled signal. These multi-bit numbers are delayed by separate circuitry, including first-in/first-out, or FIFO, memories, decimators, and phase rotators, before being summed with the separately delayed, multi-bit, in-phase and quadrature signals from each of the other transducer elements. This is a considerable amount of hardware for a conventional 128 element transducer array, and is an enormous amount of hardware when a two-dimensional transducer array having 512 elements is considered.

SUMMARY OF THE INVENTION

The present invention relates to an improved beam forming section of the receiver in an ultrasonic imaging system. More particularly, the beam forming section of the invention includes a plurality of receive channels, one for each separate transducer array element, and each receive channel includes an oversampled analog-to-digital (A/D) converter which receives the echo signal produced by its associated transducer array element and generates a corresponding digital signal at a sample rate in excess of the Nyquist criterion, means for delaying each digital signal by an amount necessary to steer a resulting receive beam in the desired direction, means for summing the digital signals to produce the digital receive beam, and decimation means for reducing the sample rate of the digital receive beam.

A general object of the invention is to simplify the beam forming circuitry in an ultrasonic system without reducing image quality. To provide the necessary delay resolution the sample rate of the A/D converter in each receive channel far exceeds the rate necessary to satisfy the Nyquist criterion. More specifically, the Nyquist criterion requires a sample rate of twice the bandwidth of the modulated ultrasonic signal, whereas the oversampled A/D converter in the preferred embodiment of the invention samples at thirty-two times the carrier frequency. As a result, the oversampled stream of digital signals can be delayed in increments of the sample period with simple shift registers, and the desired delay resolution of $\lambda/32$ is easily obtained (where $\lambda$ represents the carrier wavelength).

Another object of the invention is to provide a relatively simple and easily fabricated A/D converter for the beam former in an ultrasonic system. The oversampled A/D converter may be a sigma-delta modulator which produces a single-bit digital output signal at a very high sample rate. Such sigma-delta modulators are simple in construction and are easily implemented as part of an integrated circuit. The decimator serves as the demodulator of the single-bit digital signal.

A more specific object of the invention is to reduce the number and complexity of the delay circuits and decimators needed by the beam forming portion of an ultrasonic system. Rather than providing separate delays and separate decimators in each receive channel, the delay circuits can be partially shared with other receive channels and a single decimator may be employed after the separately delayed digital signals are summed together.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 2 is a block diagram of a transmitter which forms part of the system of FIG. 1;

FIGS. 2A and 2B are graphical illustrations of the signal in any of the channels of transmitter 50 of FIG. 2;

FIG. 3 is a block diagram of a receiver which forms part of the system of FIG. 1;

DESCRIPTION OF THE PREFERRED EMBODIMENT

Figure 1:
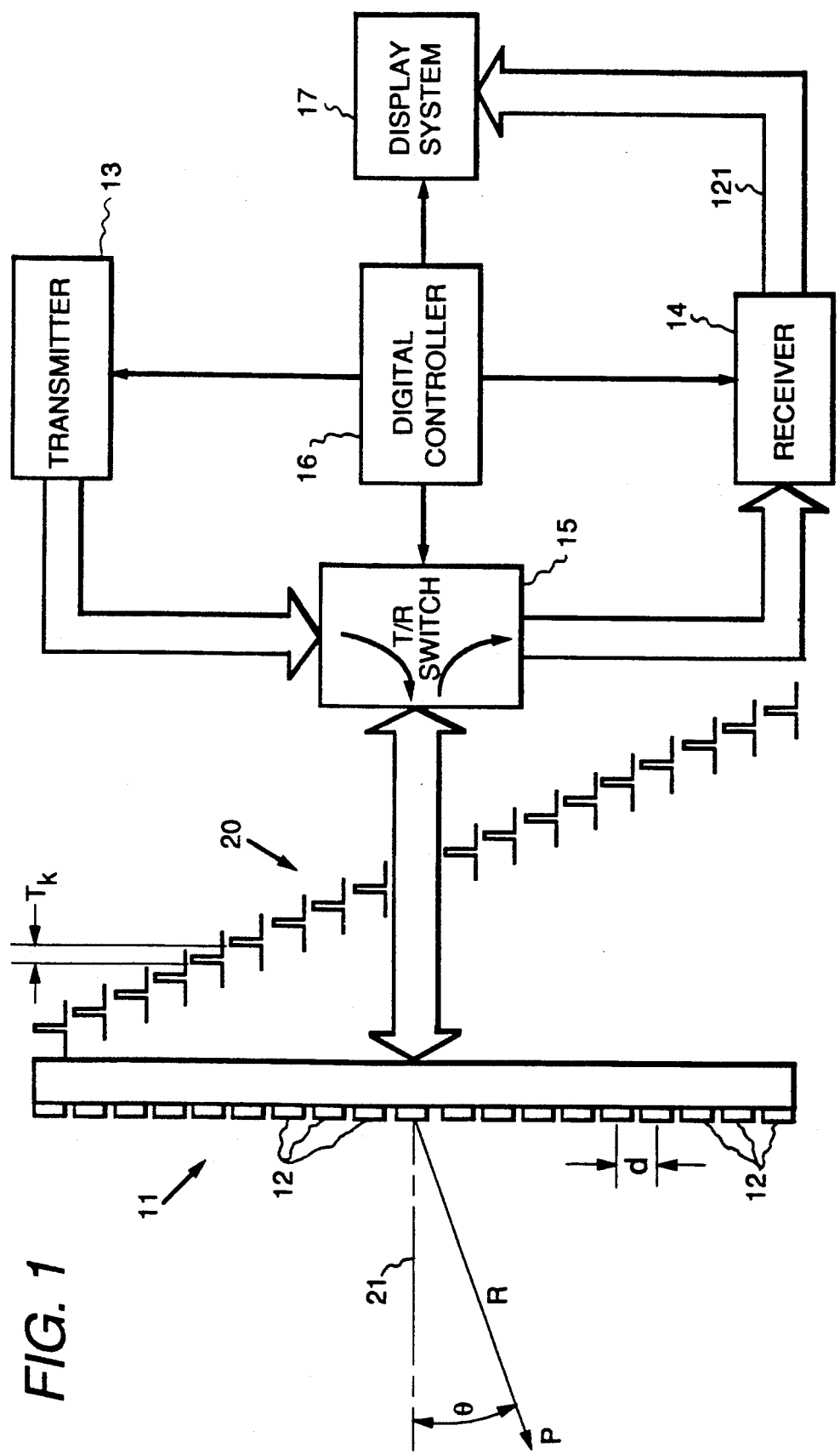
FIG. 1 is a block diagram of a vibratory imaging system which employs the present invention.

Referring particularly to FIG. 1, an ultrasonic imaging system includes a transducer array 11 comprised of a plurality of separately driven elements 12 which each produce a burst of vibratory energy, such as ultrasonic energy, when energized by a pulse produced by a transmitter 13. The vibratory energy reflected back to transducer array 11 from the subject under study is converted to an electrical signal by each transducer element 12 and applied separately to a receiver 14 through a set of switches 15. Transmitter 13, receiver 14 and switches 15 are operated under control of a digital controller 16 responsive to commands by a human operator. A complete scan is performed by acquiring a series of echoes in which switches 15 are set to their transmit positions, transmitter 13 is gated on momentarily to energize each transducer element 12, switches 15 are then set to their receive positions, and the subsequent echo signals produced by each transducer element 12 are applied to receiver 14. The separate echo signals from each transducer element 12 are combined in receiver 14 to produce a single echo signal which is employed to produce a line in an image on a display system 17.

Transmitter 13 drives transducer array 11 such that the vibratory energy produced, e.g., ultrasonic energy, is directed, or steered, in a beam. A B-scan can therefore be performed by moving this beam through a set of angles from point-to-point rather than physically moving transducer array 11. To accomplish this, transmitter 13 imparts a time delay ($T_k$) to the respective pulses 20 that are applied to successive transducer elements 12. If the time delay is zero ($T_k=0$), all the transducer elements 12 are energized simultaneously and the resulting ultrasonic beam is directed along an axis 21 normal to the transducer face and originating from the center of transducer array 11. As the time delay ($T_k$) is increased, as illustrated in FIG. 1, the ultrasonic beam is directed downward from central axis 21 by an angle $\theta$. The relationship between the time delay increment $T_k$ added successively to each $k^{th}$ signal from one end of the transducer array ($k=1$) to the other end ($k=N$) is given by the following relationship:

$$T_k = -(k-(N-1)/2)\, d \sin\theta/c + (k-(N-1)/2)^2\, d^2 \cos^2\theta/2R_T c + T_0 \qquad (1)$$

where
- $d$ = equal spacing between centers of adjacent transducer elements 12,
- $c$ = velocity of sound in the object under study.
- $R_T$ = range at which transmit beam is to be focused.
- $T_0$ = delay offset which insures that all calculated values ($T_k$) are positive values.

The first term in this expression steers the beam in the desired angle $\theta$, and the second is employed when the transmitted beam is to be focused at a fixed range. A sector scan is performed by progressively changing the time delays $T_k$ in successive excitations. The angle $\theta$ is thus changed in increments to steer the transmitted beam in a succession of directions. When the direction of the beam is above central axis 21, the timing of pulses 20 is reversed, but the formula of equation (1) still applies.

Referring still to FIG. 1, the echo signals produced by each burst of ultrasonic energy emanate from reflecting objects located at successive positions along the ultrasonic beam. These are sensed separately by each segment 12 of transducer array 11 and a sample of the magnitude of the echo signal at a particular point in time represents the amount of reflection occurring at a specific range (R). Due to differences in the propagation paths between a focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle $\theta$.

To simultaneously sum the electrical signals produced by the echoes from each transducer element 12, time delays are introduced into each separate transducer element channel of receiver 14. In the case of linear array 11, the delay introduced in each channel may be divided into two components, one component is referred to as a beam steering time delay, and the other component is referred to as a beam focusing time delay. The beam steering and beam focusing time delays for reception are precisely the same delays ($T_k$) as the transmission delays described above. However, the focusing time delay component introduced into each receiver channel is continuously changing during reception of the echo to provide dynamic focusing of the received beam at the range R from which the echo signal emanates. This dynamic focusing delay component is as follows:

$$T_k = (k-(N-1)/2)^2\, d^2 \cos^2\theta/2Rc \qquad (2)$$

where

- R = the range of the focal point P from the center of the array 11;
- c = the velocity of sound in the object under study; and
- $T_k$ = the desired time delay associated with the echo signal from the $k^{th}$ element to coherently sum it with the other echo signals.

Under direction of digital controller 16, receiver 14 provides delays during the scan such that steering of receiver 14 tracks with the direction of the beam steered by transmitter 13 and it samples the echo signals at a succession of ranges (R) and provides the proper delays to dynamically focus at points P along the beam. Thus each emission of an ultrasonic pulse results in acquisition of a series of data points which represent the amount of reflected sound from a corresponding series of points P located along the ultrasonic beam.

Display system 17 receives the series of data points produced by receiver 14 and converts the data to a form producing the desired image. For example, if an A-scan is desired, the magnitude of the series of data points is merely graphed as a function of time. If a B-scan is desired, each data point in the series is used to control brightness of a pixel in the image, and a scan comprised of a series of measurements at successive steering angles ($\theta$) is performed to provide the data necessary for display.

Referring to FIG. 2 in conjunction with FIGS. 1, 2A and 2B, transmitter 13 includes a set of channel pulse code memories which are indicated collectively as memories 50. In the preferred embodiment there are 128 separate transducer elements 12, and therefore, there are 128 separate channel pulse code memories 50. Each pulse code memory 50 is typically a 1-bit by 512-bit memory which stores a bit pattern 51, shown in FIG. 2A, that determines the frequency of ultrasonic pulse 52, shown in FIG. 2B, that is to be produced. In the preferred embodiment, the bit pattern of FIG. 2A is read out of each pulse code memory 50 by a 40 MHz master clock and applied to a driver 53 which amplifies the signal to a power level suitable for driving transducer 11. For the example shown in FIG. 2A, the bit pattern is a sequence of four "1" bits alternated with four "0" bits to produce a 5 MHz ultrasonic pulse 52. The transducer elements 11 (FIG. 1) to which these ultrasonic pulses 52 are applied respond by producing ultrasonic energy. If all 512 bits are used, a pulse of bandwidth as narrow as 40 kHz centered on the carrier frequency (i.e. 5 MHz in the example) will be emitted.

As indicated above, to steer the transmitted beam of ultrasonic energy in the desired direction ($\theta$), pulses 52 for each of the N channels, such as shown in FIG. 2B, must be delayed by the proper amount. These delays are provided by a transmit control 54 which receives four control signals (START, MASTER CLOCK, $R_T$ and $\theta$) from digital controller 16 (FIG. 1). Using the input control signal $\theta$, the fixed transmit focus $R_T$, and the above equation (1), transmit control 54 calculates the delay increment $T_k$ required between successive transmit channels. When the START control signal is received, transmit control 54 gates one of four possible phases of the 40 MHz MASTER CLOCK signal through to the first transmit channel 50. At each successive delay time interval ($T_k$) thereafter, one of the phases of the 40 MHz MASTER CLOCK signal is gated through to the next channel pulse code memory 50 until all N=128 channels are producing their ultrasonic pulses 52 (FIG. 2B). Each transmit channel 50 is reset after its entire bit pattern 51, such as shown in FIG. 2A, has been transmitted and transmitter 13 then waits for the next θ and next START control signals from digital controller 16. As indicated above, in the preferred embodiment of the invention a complete B-scan is comprised of 128 ultrasonic pulses steered in Δθ increments of 0.70° through a 90° sector centered about the central axis 21 (FIG. 1) of transducer 11.

For a detailed description of the transmitter 13, reference is made to U.S. Pat. No. 5,014,712 issued on May 14, 1991 and entitled "Coded Excitation For Transmission Dynamic Focusing of Vibratory Energy Beam", incorporated herein by reference.

Referring particularly to FIG. 3 in conjunction with FIG. 1, receiver 14 is comprised of two sections: a time-gain control section 100, and a receive beam forming section 101. Time-gain control section 100 includes an amplifier 105 for each of the N=128 receiver channels and a time-gain control circuit 106. The input of each amplifier 105 is connected to a respective one of transducer elements 12 to receive and amplify the echo signal which it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets eight (typically) TGC linear potentiometers 108 to values which provide a relatively uniform brightness over the entire range of the sector scan. The time interval over which the echo signal is acquired determines the range from which it emanates, and this time interval is divided into eight segments by TGC control circuit 106. The settings of the eight potentiometers are employed to set the gain of amplifiers 105 during each of the eight respective time intervals so that the echo signal is amplified in ever increasing amounts over the acquisition time interval.

The receive beam forming section 101 of receiver 14 includes N=128 separate receiver channels 110. As will be explained in more detail below, each receiver channel 110 receives the analog echo signal from one of the TGC amplifiers 105 at an input 111, and it produces a stream of digitized output values on a bus 112. Each of these output values represents a sample of the echo signal envelope at a specific range (R). These samples have been delayed in the manner described above such that when they are summed at summing point 114 with the output samples from each of the other receiver channels 110, they indicate the magnitude of the echo signal reflected from a point P located at range R on the steered beam (θ). These beam samples are 8-bit binary numbers which are provided at an output 121. In the preferred embodiment, each echo signal is sampled at equal intervals of about 150 micrometers over the entire range of the scan line (typically 40 to 200 millimeters).

Figure 4:
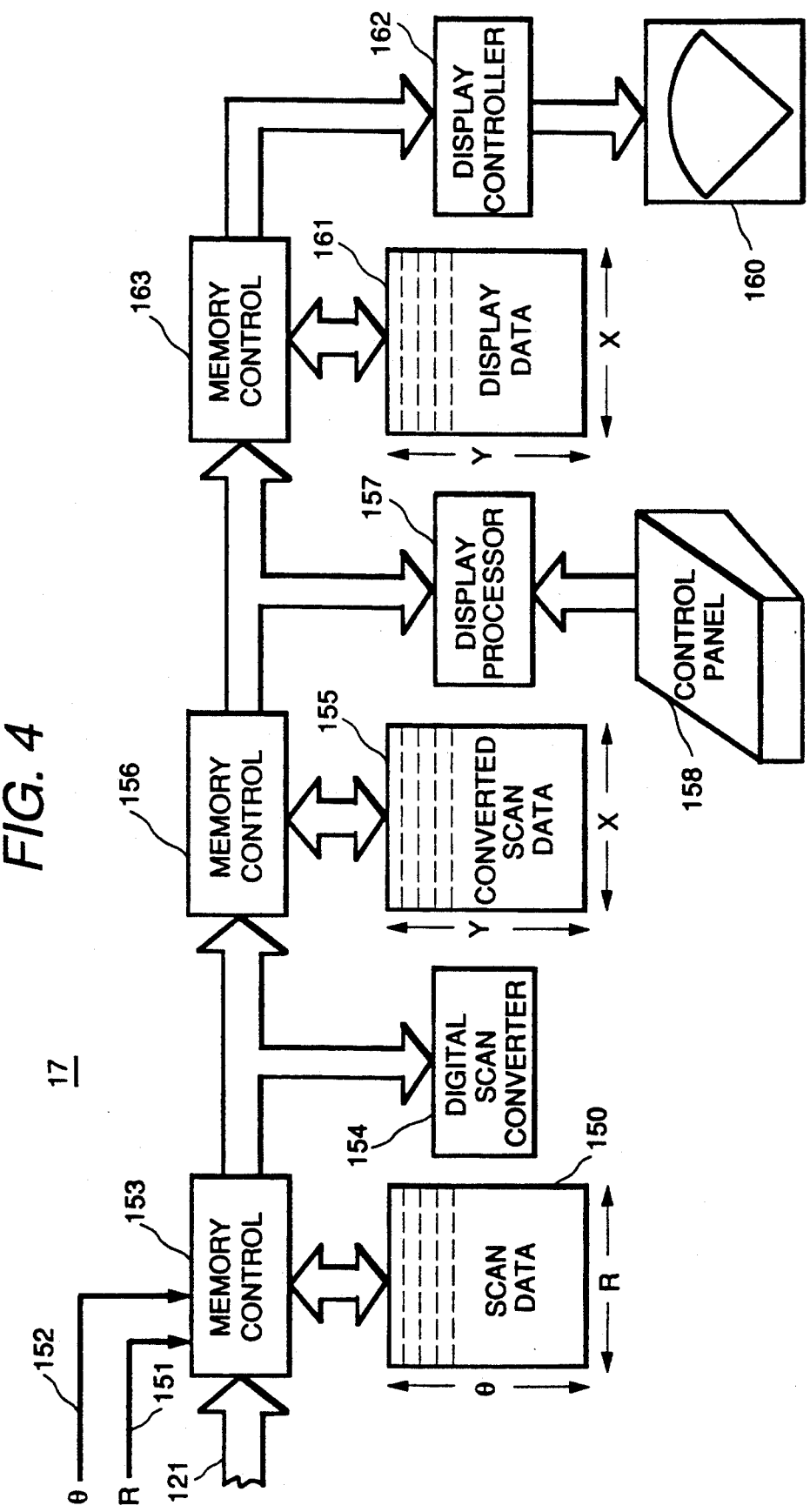
FIG. 4 is a block diagram of a display system which forms part of the system of FIG. 1.

Referring particularly to FIGS. 1 and 4, the stream of 8-bit binary numbers generated by receiver 14 at its output 121 is applied to the input of display system 17. This "scan data" is stored in a memory 150 as an array, with the rows of the scan data array 150 corresponding with the respective beam angles (θ) that are acquired, and the columns of scan data array 150 corresponding with the respective ranges (R) at which samples are acquired along each beam. The R and θ control signals 151 and 152 from receiver 14 indicate where each input value is to be stored in array 150, and a memory control circuit 153 writes that value to the proper memory location in array 150. The scan can be continuously repeated and the flow of values from receiver 14 will continuously update scan data array 150.

Referring still to FIG. 4, the scan data in array 150 are read by a digital scan converter 154 and converted to a form producing the desired image. If a conventional B-scan image is being produced, for example, the sample values M(R,θ) stored in scan data array 150 are converted to sample values M(x,y) which indicate magnitudes at pixel locations (x,y) in the image. Such a polar coordinate to Cartesian coordinate conversion of the ultrasonic image data is described, for example, in an article by Steven C. Leavitt et al in *Hewlett-Packard Journal*, October, 1983, pp. 30–33, entitled "A Scan Conversion Algorithm for Displaying Ultrasound Images".

Regardless of the particular conversion made by digital scan converter 154, the resulting image data are written to a memory 155 which stores a two-dimensional array of converted scan data. A memory control 156 provides dual port access to the memory 155 such that the digital scan converter 154 can continuously update the values therein with fresh data while a display processor 157 reads the updated data. The display processor 157 is responsive to operator commands received from a control panel 158 to perform conventional image processing functions on the converted scan data in memory 155. For example, the range of brightness levels indicated by the converted scan data in memory 155 may far exceed the brightness range of display device 160. Indeed, the brightness resolution of the converted scan data in memory 155 may far exceed the brightness resolution of the human eye, and manually operable controls are typically provided which enable the operator to select a window of brightness values over which maximum image contrast is to be achieved. The display processor reads the converted scan data from memory 155, provides the desired image enhancement, and writes the enhanced brightness values to a display memory 161.

Display memory 161 is shared with a display controller circuit 162 through a memory control circuit 163, and the brightness values therein are mapped to control brightness of the corresponding pixels in display 160. Display controller 162 is a commercially available integrated circuit which is designed to operate the particular type of display 160 used. For example, display 160 may be a CRT (cathode ray tube), in which case display controller 162 is a CRT controller chip which provides the required sync pulses for the horizontal and vertical sweep circuits and maps the display data to the CRT at the appropriate time during the sweep.

It should be apparent to those skilled in the art that display system 17 may take one of many forms depending on the capability and flexibility of the particular ultrasound system. In the preferred embodiment described above, programmed microprocessors are employed to implement the digital scan converter and display processor functions, and the resulting display system is, therefore, very flexible and powerful.

Figure 5:
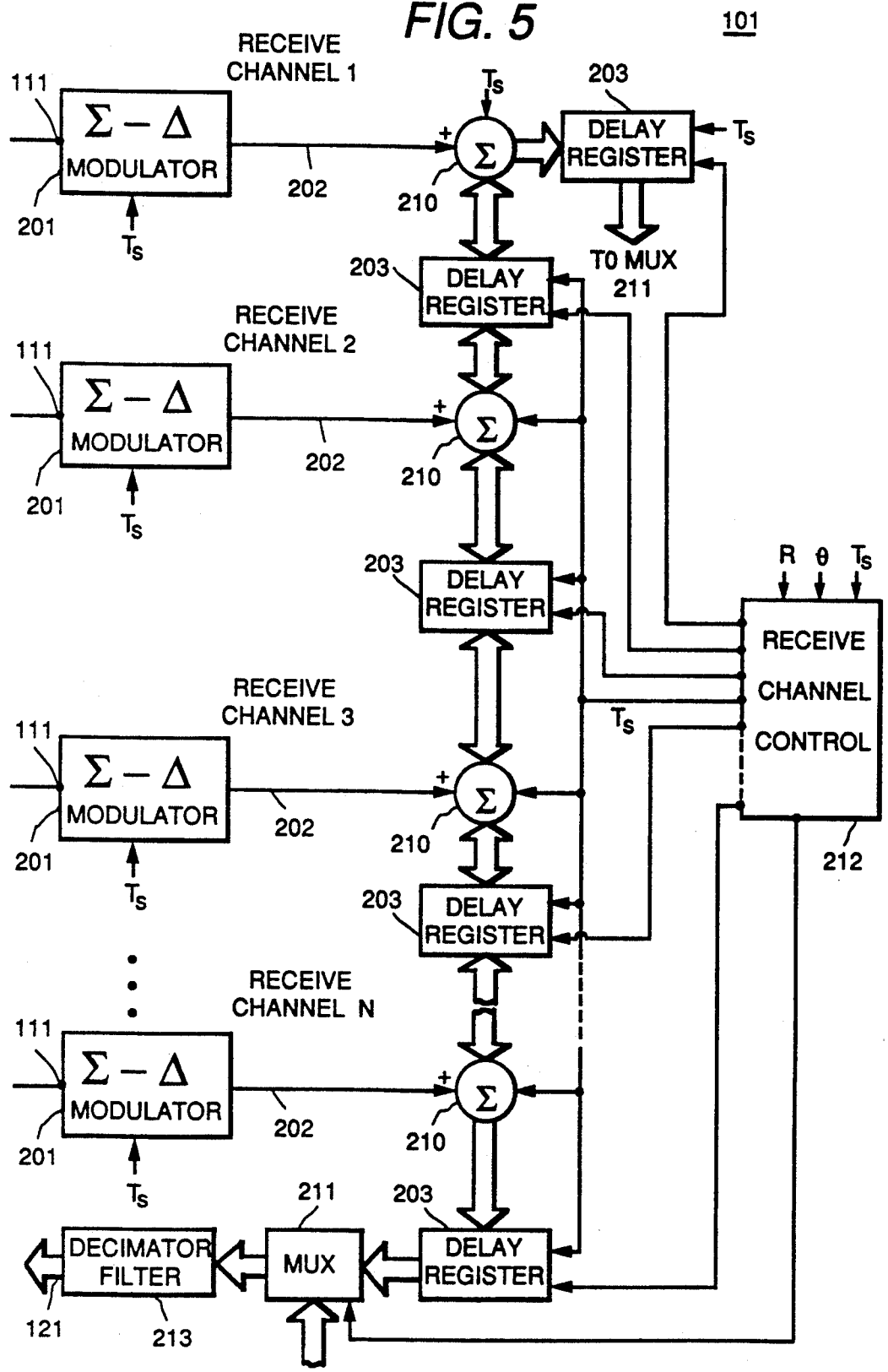
FIG. 5 is a block diagram of a preferred embodiment of the beam former of the present invention which forms part of the receiver of FIG. 3.

As indicated above with reference to FIG. 3, beam forming section 101 of receiver 14 is comprised of a set of receiver channels 110—one for each element 12 of transducer 11. Referring particularly to FIG. 5, the beam former is responsive to a 160 MHz master clock ($T_s$), a range signal (R) and a beam steering angle signal ($\theta$) from digital controller 16 (FIG. 1) in order to perform the digital beam forming functions. The analog input signal from each transducer element 12 is applied to the input 111 of a corresponding sigma-delta ($\Sigma\Delta$) modulator 201 and is converted thereby to a one-bit digital signal at its output 202. Such modulators, as is well known in the art, are characterized by simplicity of construction and operation when compared to conventional multi-bit analog-to-digital converters. The sigma-delta modulator samples the analog echo signal at the 160 MHz rate of the clock $T_s$, which is thirty-two times the 5 MHz carrier frequency of the ultrasound echo signal and sixteen times the Nyquist sample rate normally applicable to multi-bit A/D converters.

Oversampling of the analog echo signal accomplishes two objectives. First, the digital output signal of each modulator 201 is a single-bit, which is easily processed, and second, each bit supplied by a modulator 201 represents a sample of the echo signal over a very small increment of time (6.25 nanoseconds). The resulting single-bit digitized signal can, therefore, be delayed in very small increments of time in delay registers 203 to provide a high resolution means for delaying the echo signals from each transducer element 12 (FIG. 1).

Delay registers 203 are coupled together in a chain and the single-bit signal from each transducer element 12 produced by its corresponding modulator 201 is inserted into this chain by respective summing circuits 210. Each delay register 203 is a conventional variable-delay shift register 80 stages in length and the digital signals are shifted through their stages by a 160 MHz master clock signal $T_s$. The desired time delay for each register 203 is determined by the location of the shift register stage from which the digital echo signal is produced. For example, if the delay is calculated to be 125 nanoseconds, then the echo signal is shifted through the first 125/6.25=20 stages of the delay register 203. It can be appreciated, therefore, that the desired high resolution time delay is achieved with a very simple and easily constructed device.

The beam former summing circuits 210 are binary adders which arithmetically sum each single-bit digital signal from its associated sigma-delta modulator 201 with the multi-bit binary number representing the number of "1s" produced by the "upstream" receiver channels during the clock period $T_s$. The delay registers 203 are coupled between successive summing circuits 210 and are separately controlled by a receive channel control 212 to provide the proper time delay. The total delay imposed on any receive channel echo signal, therefore, is the sum of all the delays in those of delay registers 203 which are "downstream" of the point at which the echo signal is added to the chain. The time delay provided by each register 203 is equal to the delay as determined by equation (1) for the associated transducer element number, minus all the delays imposed by the "downstream" delay registers 203. The widths of delay registers 203 increase as one moves "downstream", with the number of width bits for each register equal to $\log_2$ of the total number of receive channels summed together at its input. For example, the width of the last delay register 203 before the decimator filter 213 is:

$$\text{WIDTH } (W) = \log_2 (N)$$

where N is the total number of array elements 12. This width formula is also applicable to summing circuits 210 and decimator filter 213.

The direction in which echo signal data flows through the chain of summing circuits 210 and delay registers 203 is determined by the steering angle $\theta$ and is controlled by receive channel control 212. As the steering angle $\theta$ is increased in one direction from central axis 21 (FIG. 1), the delay on receive channel 1 is greater than the delay on receive channel N and data flows downward through the chain. On the other hand, as the steering angle $\theta$ is increased in the opposite direction from central axis 21, the delay on receive channel N is greater and the data flows upward through the chain. The summing circuits are of the type in which at least one input and one output are interchangeable with each other. The outputs of delay registers 203 at each end of the chain are coupled to input channels of a multiplexer 211, and receive channel control 212 selects which delay register output signal will be applied to a decimator filter 213.

Decimator filter 213 is a multi-bit low pass filter which filters out the high frequency quantization noise introduced by sigma-delta modulators 201. In addition, a frequency decimation is simultaneously performed to sample down the 160 MHz oversampled frequency to a more conventional 5 MHz sample rate. While a conventional equiripple finite impulse response ("FIR") decimation filter such as that described by E. Dijkstra et al. in "A Design Methodology For Decimation Filters In Sigma-Delta A/D Converters", *ISCAS* 87, pp. 479–482 (1987) may be used, a one-stage Comb decimation filter such as that described by E. Dijkstra et al. in "On The Use of Modulo Arithmetic Comb Filters In Sigma-Delta Modulators", *IEEE*, pp. 2001–2004 (1988) is preferred. Both of these Dijkstra et al. papers are herein incorporated by reference. Decimator filter 213 produces 16-bit samples $S(R,\theta)$ of steered and focused receive beam data at a 5 MHz sample rate which are provided through bus 121 to display 17 (FIG. 1).

Figure 6:
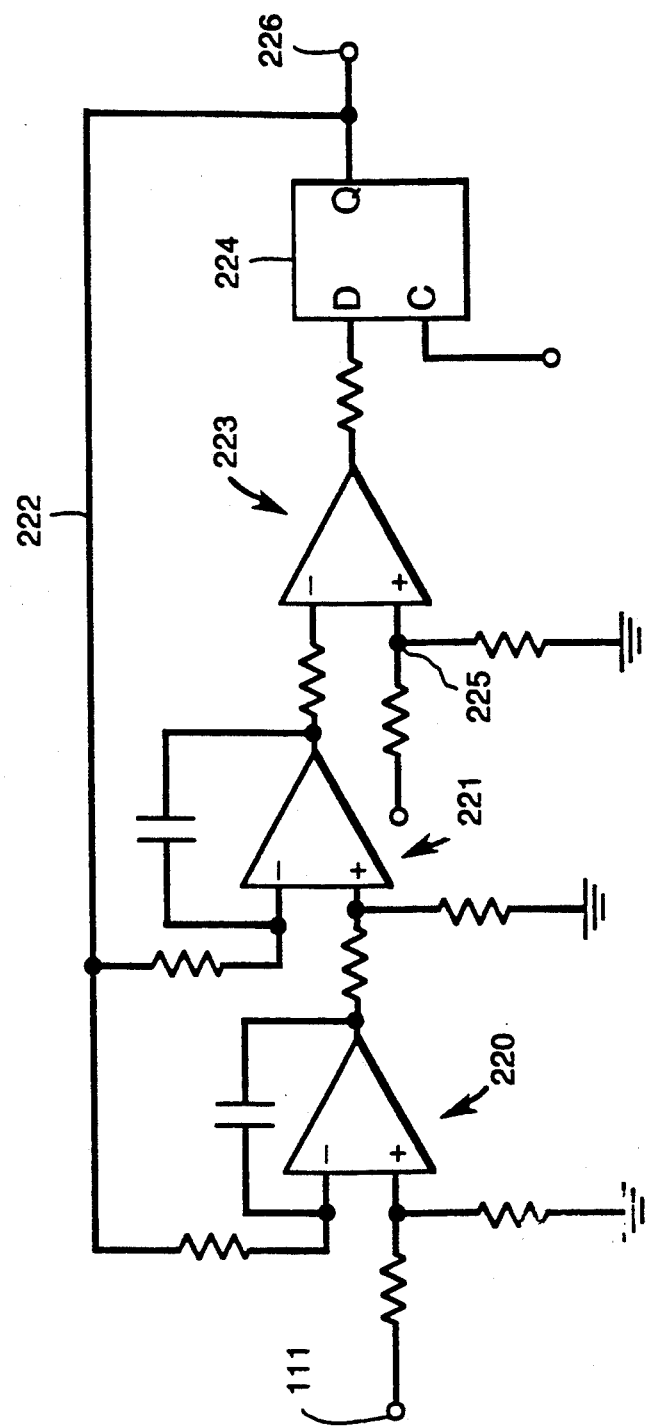
FIG. 6 is a circuit diagram of a preferred sigma-delta modulator used in the beam former of FIG. 5.

Sigma-delta modulators are well known in the art of communications and there are many different circuits which may be employed successfully in the present invention. See, for example, D. B. Ribner et al. U.S. Pat. No. 5,065,157, issued Nov. 12, 1991 and assigned to the instant assignee. The Ribner et al. patent is herein incorporated by reference. The preferred circuit, shown in FIG. 6, is a second order sigma-delta modulator, which includes two serially connected integrators 220 and 221 which receive the analog input signal at input 111. The analog input signal is applied to the non-inverting input of each integrator 220 and 221, while a feedback signal on line 222 is applied to the inverting input of each integrator 220 and 221. The output of the second integrator 221 is applied to the input of a comparator circuit 223 which produces either a logic high voltage or a logic low voltage at its output. This logic level signal is applied to the D input of a D-type flip-flop 224 which is clocked by the master clock signal $T_s$ every 6.25 nanoseconds.

As the echo signal applied to input 111 rises in value the output signals of integrators 220 and 221 follow. When this voltage increase exceeds a reference value established at the negative input 225 of comparator 223, the comparator output switches to a logic high voltage. On the next clock pulse $T_s$, therefore, flip-flop 224 is set and produces a logic high voltage at the delta-sigma modulator output 226 and on feedback line 222. The logic high voltage on feedback line 222 supplies a current to each integrator 220 and 221 which precisely offsets the rise in input voltage and drives the integrator output signals back to zero. Unless the input voltage continues to rise during the next clock period, therefore, the comparator output will be at a logic low voltage when the next clock signal $T_s$ is applied to the flip-flop 224, and a logic low, or "0" will be produced at output 226. The signal at output 226 of the delta-sigma modulator is thus a stream of "1"s and "0"s with each "1" representing an incremental increase in the echo signal and each "0" representing an incremental decrease in the echo signal.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. In a vibratory energy imaging system which includes a vibratory energy transducer having a set of N elements that produce N separate echo signals, a beam former for separately delaying and summing the N echo signals to produce a digital beam signal, comprising:
    a set of N oversampled analog-to-digital converters, each one of said converters being coupled to receive a respective one of the N echo signals and each being operable to produce a digitized representation of its respective echo signal at a sample rate in excess of the sample rate required to meet the Nyquist criterion;
    delay means for separately delaying each digitized representation of an echo signal in increments corresponding to said sample rate;
    summing means for arithmetically adding together the digitized and delayed representations of the N echo signals; and
    decimator means for reducing the sample rate of said digitized representation of said N echo signals to the rate required to meet the Nyquist criterion.

2. The beam former as recited in claim 1 in which each of the N oversampled analog-to-digital converters is adapted to produce a one-bit wide digitized representation of its respective echo signal.

3. The beam former as recited in claim 2 in which the delay means comprises a register means which stores at successive register locations thereof successive samples of the digitized representations of the echo signals.

4. The beam former as recited in claim 3 wherein the summing means comprises a plurality of summing circuits, each of said summing circuits being coupled to said register means at two successive register locations, respectively, said summing circuits summing together the digitized representations of the N respective echo signals to form a digitized representation of the sum of said N echo signals, said decimator means being coupled to said register means for receiving said digitized representation of the sum of said N echo signals and reducing the sample rate thereof.

5. The beam former as recited in claim 3 including multiplexer means for coupling one of two ends of said register means to said decimator means.

6. The beam former as recited in claim 1 in which each of the N oversampled analog-to-digital converters comprises a sigma-delta modulator.

7. The vibratory energy imaging system of claim 1 wherein said vibratory energy comprises ultrasonic energy and said vibratory energy transducer comprises an ultrasonic transducer.

8. In a vibratory energy imaging system which includes a vibratory energy transducer having a set of N elements that produce N separate echo signals, a beam former for separately delaying and summing the N echo signals to produce a digital beam signal, comprising:
    a set of N single-bit analog-to-digital converters, each one of said converters being coupled to receive a respective one of the N echo signals and being operable to produce a digitized representation of its respective echo signal at a high sample rate;
    a set of delay register means, each one of said delay register means being operable to receive at an input a digitized representation of an echo signal at the high sample rate, and being operable to produce at an output a delayed digitized representation of an echo signal previously applied to its input;
    a set of summing means interconnected with the set of delay register means to form a chain in which one input of each summing means is coupled to an output of a respective one of the delay register means, an output of said each summing means is coupled to the input of the next respective one of the delay register means in the chain, and a second input of said each summing means is coupled to receive the digitized representation of an echo signal from a respective one of said single-bit analog-to-digital converters, wherein said each summing means is operable to arithmetically add a delayed digitized representation of an echo signal applied to its one input to the digitized representation of an echo signal applied to its second input and produce a resulting digitized representation of an echo signal at its output; and
    decimator means coupled to the output of the delay register means at an end of said chain to receive a delayed digitized representation of an echo signal at said high sample rate and being operable to produce at an output a digital beam signal at a lower sample rate.

9. The beam former as recited in claim 8 including multiplexer means coupling the output of said delay register means at said end of said chain to said decimator means.

10. The beam former as recited in claim 8 in which the decimator means includes a digital low pass filter for filtering out high frequency quantization noise introduced by the single-bit analog-to-digital converters.

11. The beam former as recited in claim 10 wherein, in said each summing means, the output and the second input are interchangeable with each other so as to permit reversal of the order in which the digitized signals produced by the single-bit analog-to-digital converters are applied to the chain.

12. The apparatus of claim 7 wherein said vibratory energy comprises ultrasonic energy and said vibratory energy transducer comprises an ultrasonic transducer.

* * * * *